US010907201B2

(12) United States Patent
Horton et al.

(10) Patent No.: US 10,907,201 B2
(45) Date of Patent: *Feb. 2, 2021

(54) DIRECT NUCLEIC ACID AMPLIFICATION KIT, REAGENT AND METHOD

(71) Applicant: Global Life Sciences Solutions Operations UK Ltd, Sheffield (GB)

(72) Inventors: Jeffrey K. Horton, Cardiff (GB); Peter J. Tatnell, Cardiff (GB); Kathryn L. Lamerton, Cardiff (GB)

(73) Assignee: Global Life Sciences Solutions Operations UK Ltd, Sheffield (GB)

( * ) Notice: Subject to any disclaimer, the term of this patent is extended or adjusted under 35 U.S.C. 154(b) by 359 days.

This patent is subject to a terminal disclaimer.

(21) Appl. No.: 15/432,476

(22) Filed: Feb. 14, 2017

(65) Prior Publication Data
US 2017/0152546 A1 Jun. 1, 2017

Related U.S. Application Data

(62) Division of application No. 13/799,800, filed on Mar. 13, 2013, now abandoned.

(30) Foreign Application Priority Data

Oct. 24, 2012 (GB) .................................. 1219137.5

(51) Int. Cl.
*C12Q 1/68* (2018.01)
*C12Q 1/686* (2018.01)
*C12P 19/34* (2006.01)

(52) U.S. Cl.
CPC .............. *C12Q 1/686* (2013.01); *C12P 19/34* (2013.01); *C12Q 2527/125* (2013.01)

(58) Field of Classification Search
None
See application file for complete search history.

(56) References Cited

U.S. PATENT DOCUMENTS

| | | | |
|---|---|---|---|
| 5,565,318 A | 10/1996 | Walker et al. | |
| 5,705,345 A | 1/1998 | Lundin et al. | |
| 5,972,386 A | 10/1999 | Burgoyne | |
| 7,462,475 B2 | 12/2008 | Kermekchiev et al. | |
| 8,153,401 B2 | 4/2012 | Chang et al. | |
| 8,173,401 B2 | 5/2012 | Chang et al. | |

| | | | |
|---|---|---|---|
| 2006/0160078 A1 * | 7/2006 | Cardy | ................... B01L 3/5023 435/6.11 |
| 2011/0256592 A1 | 10/2011 | Beckers et al. | |
| 2014/0113294 A1 | 4/2014 | Horton et al. | |

FOREIGN PATENT DOCUMENTS

| | | | |
|---|---|---|---|
| CN | 101516337 A | 8/2009 | |
| WO | 99/38962 A2 | 8/1999 | |
| WO | 2008/036544 | 3/2008 | |
| WO | WO-2008144556 A1 * | 11/2008 | ........... C12Q 1/6806 |
| WO | WO-2010002938 A2 * | 1/2010 | ........ C12Q 2527/125 |
| WO | 2010/066908 | 6/2010 | |
| WO | WO-2010066908 A1 * | 6/2010 | ........... C12Q 1/6848 |

OTHER PUBLICATIONS

GE Healthcare (Nucleic Acid Sample Preparation for Downstream Analyses, attached, Oct. 2009).*
Chinese Office Action for CN Application No. 201380055445.3 dated Aug. 1, 2017 (27 pages).
Japanese Office Action for JP Application No. 2015-538433 dated Sep. 19, 2017 (6 pages).
Chinese Office Action for CN Application No. 201380055445.3 dated Apr. 28, 2016.
Bustin, S., et al., Journal of Biomolecular Techniques, vol. 15, issue 3, pp. 155-166 (2004).
Muzzio, F., et al., Powder Technology, 124 (2002) pp. 1-7.
Palepu, R., et al., Can. J. Chem., vol. 66 (1988) pp. 325-328.
Ratti, C., Journal of Food Engineering, vol. 49 (2001) pp. 311-319.
Rubino, 0., Pharmaceutical Technology, Jun. 1999, pp. 104-113.
Tang, X., et al., Pharmaceutical Research, vol. 21, No. 2 (2004) pp. 191-200.
Search Report dated Feb. 19, 2013 issued on corresponding GB patent application No. 1219137.5.
International Search Report dated Dec. 10, 2013 issued on corresponding patent application No. PCT/EP2013/072206.
European Office Action for EP Application No. 13779893.0 dated Feb. 27, 2018 (6 pages).
Japanese Office Action for JP Application No. 2018-128740 dated Jun. 13, 2019 (8 pages, English translation).
Japanese Office Action for JP Application No. 2018-128740 dated Sep. 25, 2019 (8 pages, English translation).

* cited by examiner

*Primary Examiner* — Aaron A Priest
(74) *Attorney, Agent, or Firm* — Eversheds Sutherland (US) LLP

(57) ABSTRACT

The present invention relates to compositions, methods and kits which can be used to amplify nucleic acids with the advantage of decreasing user time and possible contamination. The dried reagent composition of the invention can be used for easy processing and amplification of nucleic acid samples.

12 Claims, 3 Drawing Sheets

Specification includes a Sequence Listing.

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ttaggcctta gcgggcttag ac                                               22

<210> SEQ ID NO 2
<211> LENGTH: 22
<212> TYPE: DNA
<213> ORGANISM: Artificial
<220> FEATURE:
<223> OTHER INFORMATION: PCR primer

<400> SEQUENCE: 2
ccaggatttt tgatgggaca cg                                               22
```

DIRECT NUCLEIC ACID AMPLIFICATION KIT, REAGENT AND METHOD

CROSS REFERENCES TO RELATED APPLICATIONS

This patent application is a divisional of U.S. application Ser. No. 13/799,800, filed Mar. 13, 2013, which claims priority benefit of U.K. Application No. 1219137.5, filed Oct. 24, 2012, each of which are incorporated herein by reference in their entireties.

FIELD OF INVENTION

The present invention relates to the field of nucleic acid amplification, particularly to the use of a polymerase chain reaction to amplify nucleic acids. The invention provides methods and kits which can be used to amplify nucleic acids by lyophilizing or freeze-drying nucleic acid amplification reagents for easy amplification of nucleic acid samples. The invention has applications in the easy processing of nucleic acids and is particularly useful in genotyping, diagnostics and forensics.

BACKGROUND TO THE INVENTION

The polymerase chain reaction (PCR) is a common tool used in molecular biology for amplifying nucleic acids. U.S. Pat. No. 4,683,202 (Mullis, Cetus Corporation) describes a process for amplifying any desired specific nucleic acid sequence contained in a nucleic acid or mixture thereof.

U.S. Pat. No. 5,705,345 (Lundin et al.) describes a method of nucleic acid preparation whereby the sample containing cells is lysed to release nucleic acid and the sample is treated with cyclodextrin to neutralize the extractant. The advantage of this system is that conventional detergent removal requires a separation step; however the addition of cyclodextrin to neutralize the detergent removes the need for the separation step and thus reduces the risk of contamination.

WO9938962 (Health, Gentra Systems Inc.) describes a solid support with a bound lysis reagent. The lysis reagent can comprise a detergent, a chelating agent, water and optionally an RNA digesting enzyme. The method for PCR amplification requires further steps for purification of the nucleic acid for amplification analysis.

WO9102040 (Kosak) describes an invention using cyclodextrin-labelled primers in an amplification reaction mixture for qualitative and quantitative nucleic acid sequence analysis. The benefits of this invention are a higher signal efficiency and versatility in label colours.

WO9532739 (Agrawal) describes an oligonucleotide non-covalently complexed with a cyclodextrin. However the incorporation of cyclodextrin with oligonucleotides was for the cellular uptake of oligonucleotides and not for the amplification of nucleotides in a PCR reaction.

WO2010066908 (Beckers et al.,) describes the use of cyclodextrins to improve the specificity, sensitivity and/or yield of PCR. The method discloses an amplification reaction which is performed in a reaction mixture comprising at least one cyclodextrin and performing the amplification reaction on the reaction mixture. The PCT application discloses kits for the amplification of a target nucleic acid in a sample comprising in the same container at least a cyclodextrin and at least one component from a list of PCR reagents. The application also discloses that the kits may be provided as pre-mixes comprising several components, which may also be provided in a dehydrated, lyophilised form. However, there are no examples of such lyophilised, pre-mixed kits in the application or indeed how such kits could be prepared.

Current methods for DNA amplification involve a DNA purification procedure which often involves several steps which increases the chance of contamination. This is a tedious process and prior art methods have a number of clear disadvantages in terms of cost, complexity and in particular, user time. For example, column-based nucleic acid purification is a typical solid phase extraction method to purify nucleic acids. This method relies on the nucleic acid binding through adsorption to silica or other supports depending on the pH and the salt content of the buffer. Examples of suitable buffers include Tris-EDTA (TE) buffer or Phosphate buffer (used in DNA microarray experiments due to the reactive amines). The purification of nucleic acids on such spin columns includes a number of complex and tedious steps. Nucleic acid purification on spin columns typically involves three time-consuming and complex steps/stages: the sample containing nucleic acid is added to the column and the nucleic acid binds due to the lower pH (relative to the silanol groups on the column) and salt concentration of the binding solution, which may contain buffer, a denaturing agent (such as guanidine hydrochloride), Triton X-100, isopropanol and a pH indicator; the column is washed with 5 mM $KPO_4$ pH 8.0 or similar, 80% EtOH); and the column is eluted with buffer or water.

Alternative methods involve the binding of nucleic acids in the presence of chaotropic agents such that DNA binds to silica or glass particles or glass beads. This property was used to purify nucleic acid using glass powder or silica beads under alkaline conditions. Typical chaotropic agents include guanidinium thiocyanate or guanidinium hydrochloride and recently glass beads have been substituted with glass containing minicolumns.

Some of the pitfalls of quantitative real-time reverse transcription polymerase chain reaction, including the effect of inhibitors, are described by Bustin & Nolan (J. Biomolecular Techniques, 2004, 15, 155-166).

The best defence against PCR amplification failure in forensics applications is to combine sound sample handling and processing techniques with extraction systems proven to efficiently purify DNA.

Typically PCR reagents are stored in glycerol solution which must be maintained at temperatures below room temperature. Lyophilisation or freeze drying is a process widely used in the preparation of reagents for nucleic acid analysis and other biological processes because it allows for long term stability of otherwise labile biomolecules, and provides a convenient method of storage, shipping and reconstitution. However there are numerous technical challenges involved in producing a lyophilised or freeze-dried reagent for PCR analysis. Current technology for producing dry biological reagent compositions involves procedures such as dry-blending, spray-drying, freeze-drying, fluidized bed drying, and/or cryogenic freezing. All of these procedures have limitations and drawbacks including consistency and reliability.

With dry-blending technology (Muzzio et al 2002, Powder Technology 124, 1-7), it is often difficult to obtain homogeneous blends of chemicals due to their different densities. Furthermore, homogeneity is especially difficult to achieve when very small amounts of ingredients are mixed with large amounts of other ingredients. Even if homogeneity is achieved, it is difficult to reproducibly dispense small amounts of the blended biological chemicals.

Spray-drying technology (U.S. Pat. No. 4,712,310) provides more homogeneous blends of chemicals because the reagents are first dissolved in solution. With spray-drying, however, it is difficult to dispense precise amounts of blended chemicals. To overcome this drawback, the resulting particles are usually reprocessed by agglomeration to obtain uniform particle sizes such as tablets. However, the agglomerated particles are generally less soluble than the original spray-dried particles or powders. Also, these procedures sometimes use fluorocarbon cryogenic solutions which can be hazardous to the environment.

Fluid bed technology (Rubina, 1999, Pharmaceutical Technology, 23, 104-113) relies upon spraying a liquid reagent blend onto a particle and drying the liquid to obtain a particle coated with the blended reagents. Using this procedure, it is difficult to obtain uniformly sized particles and to produce a uniform coating.

Another method for stabilizing biologics is freeze-drying. One drawback to the freeze-drying is the use of fluorocarbon refrigerants which are difficult to dispose of and the freeze-drying process may be imprecise and also difficult to regulate. Indeed, regular freeze drying of reagents may not provide an entire solution for particularly labile reagents used in molecular biology processes. Furthermore, degradation of the product during the freeze drying process is common and a freeze dried product is not always perfectly stable during storage. Process control is critical and can be difficult to regulate (Tang & Pakil, 2004, Design of Freeze-Drying Processes for Pharmaceuticals: Practical Advice; *Pharmaceutical Research*, 21, 191-200).

Another method of stabilizing biologics is by air-drying biological reagent compositions (Ratti, 2001, Hot Air and Freeze-Drying of High Value Foods: A Review. J. *Food Engineering* 49, 311-319). Some problems with air drying processes are that the dried product is not in a readily dispensable form. Also, the biological reagents must be stable at or above the temperature of the drying process and it is a difficult process to control accurately.

One specialized process using freeze-drying technology is the formation of droplets or spheres which are contacted with a cryogenic liquid and then freeze-dried. One drawback of this technology is that the reagent spheres are fragile and tend to disintegrate.

One type of carrier or filler which has been used to stabilize biological reagents are glass-forming filler materials (U.S. Pat. No. 5,565,318). The biological reagent solutions are incorporated into the glass-forming filler materials (which are water soluble or a water-swellable substance). They are then dried to produce a glassy composition which immobilizes and stabilizes the biological reagent (U.S. Pat. No. 5,593,824).

Carbohydrates such as glucose, sucrose, maltose or maltotriose are an important group of glass-forming substances. Other polyhydroxy compounds can be used such as carbohydrate derivatives like sorbitol and chemically modified carbohydrates. Another important class of glass-forming substances are synthetic polymers such as polyvinyl pyrrolidone, polyacrylamide, or polyethyleneimine.

Further examples of glass-forming substances include sugar copolymers such as Ficoll (U.S. Pat. No. 3,300,474). Ficoll is a neutral, highly branched, high-mass, hydrophilic polysaccharide which dissolves readily in aqueous solutions. Ficoll radii range from 2-7 nm. It is prepared by reaction of the polysaccharide with epichlorohydrin. Ficoll has molecular weights of between 5,000 to 1,000,000 and contains sucrose residues linked through ether bridges to bifunctional groups. Such groups may be an alkylene of 2, 3 or more carbon atoms but not normally more than 10 carbon atoms. The bifunctional groups serve to connect sugar residues together. These polymers may, for example, be made by the reaction of sugar with a halohydrin or bis-epoxy compound. A glass is typically defined as an undercooled liquid with a very high viscosity, One drawback of the aforementioned references is that normally the stabilized and glassified biological materials are ground into powders, compounded into tablets, or maintained in a thin glassy film in a container like a microtitre plate. Numerous methods to make and use compositions of glassy immobilized biological materials have been tried. One system utilises a thin glassy film dried and dispensed into a container suitable to the final user, such as a micro centrifuge tube. However, this process has resulted only in limited success.

There is therefore a need for an improved and simplified process for performing polymerase chain reaction from samples prior to nucleic acid amplification by PCR. Furthermore, there is a need for PCR reagent mixtures which can be stored, shipped and reconstituted at room temperature without the need for storage in glycerol and lower temperatures. The present invention addresses these problems and provides methods and kits which can be used for single step amplification of nucleic acid.

SUMMARY OF THE INVENTION

The present invention provides methods and kits which can be used to amplify nucleic acids by incorporating all the required PCR reagents into a lyophilized format for easy amplification of nucleic acid samples.

According to a first aspect of the present invention there is provided a dried reagent composition for nucleic acid amplification comprising, a sequestering reagent, a polymerase and a deoxyribonucleotide triphosphate (dNTP). The advantage of incorporating the sequestrant with the polymerase and dNTP into a dried reagent composition is to reduce the number of steps required for nucleic acid amplification, thus saving operator time and facilitating operator usage.

In one aspect, the nucleic acid is selected from the group consisting of DNA, RNA and oligonucleotide.

The term "nucleic acid" is used herein synonymously with the term "nucleotides" and includes DNA, such as plasmid DNA and genomic DNA; RNA, such as mRNA, tRNA, sRNA and RNAi; and protein nucleic acid, PNA.

In another aspect, the sequestering agent is a cyclodextrin. The cyclodextrin may be selected from a group consisting of α-cyclodextrin, β-cyclodextrin, γ-cyclodextrin and derivatives thereof. Cyclodextrin could consist of a group consisting of 6-O-α-D-Maltosyl-β cyclodextrin, hydroxyethyl-β-cyclodextrin, hydroxypropyl-β-cyclodextrin and 2-hydroxypropyl-3-cyclodextrin. The sequestrant is preferably α-cyclodextrin. The sequestering reagent is not a chelating agent. A chelating agent is a chemical compound that combines with a metal to form a chelate, often used to trap heavy metal ions (Collins English Dictionary, © HarperCollins Publishers 2003). One example of a lysis reagent is sodium dodecyl suphate; sodium is a metal ion however according to Ramamurthy Palepu and Vincent C. Reinsborough (Can J. Chem Vol 66, 325-328, 1988) it is the hydrophobic tail that interacts with the cyclodextrin not the hydrophilic head.

In a further aspect, the dried reagent composition comprises at least one primer.

In a further aspect, the dried reagent composition additionally comprises an excipient mix.

The term "excipient mix" is used herein to denote additives or ingredients used to make up a preparation or mixture and for example may comprise of PCR buffer, Ficoll 70, Ficoll 400, Melezitose, Trehalose, stabilising proteins and nuclease free water.

The term "PCR buffer" is used herein to denote a buffer necessary to create optimal conditions for activity of a DNA polymerase and for example may comprise of Tris-HCl, KCl, MgCl2, gelatin and nuclease free water.

In a further aspect, the dried reagent composition additionally comprises an exchange buffer.

The term "exchange buffer" is used herein to denote a buffer used for the removal of small ionic solutes, whereby one buffer is removed and replaced with another alternative buffer and for example may comprise of Tris/HCl, CaCl2, a detergent, RE960, MgCl2, KCl and nuclease free water.

In a further aspect, the dried reagent composition additionally comprises bovine serum albumin (BSA).

In one aspect, the polymerase is an OmniKlen Taq (OKT) Polymerase. Alternatively, the polymerase may be selected from the group consisting of T4 DNA Polymerase, Pol I and Klenow Fragment, T4 DNA Polymerase, Modified Bacteriophage T7 DNA Polymerase, Terminal Deoxynucleotide Transferase, Bst Polymerase, Taq Polymerase, Tth polymerase, Pow Polymerase, Vent Polymerase, Pab Pol I DNA Polymerase, *Thermus thermophiles, Carboxydothermus hydrogenoformans*, SP6 and SP7 RNA polymerase.

In a further aspect, the preferred embodiment is a dried reagent composition comprising α-cyclodextrin, at least one primer, a polymerase, dNTP, BSA, an excipient mix and an exchange buffer.

According to a second aspect of the present invention, there is provided a method for producing a dried reagent composition for nucleic acid amplification comprising the steps:
  i) combining a polymerase with a sequestering reagent and dNTP, to provide a mixture thereof, and
  ii) drying said mixture to form a dried reagent composition.

In one aspect, the mixture additionally comprises at least one primer.

In another aspect, the mixture additionally comprises an excipient mix.

In a further aspect, the mixture additionally comprises an exchange buffer.

In one aspect, the drying step is achieved by lyophilizing the mixture.

In another aspect, the additionally comprises the step of freezing the composition prior to the drying step.

According to a third aspect of the present invention, there is provided a method for amplification of nucleic acid comprising the steps:
  i) incubating a solution containing nucleic acid with the dried reagent composition described above and,
  ii) amplifying the nucleic acid.

In one aspect, the amplification method is a polymerase chain reaction.

In another aspect, the amplification method comprises reverse transcription polymerase chain reaction or isothermal amplification.

In a further aspect, prior to step i), the solution is formed by adding water to the nucleic acid.

In one aspect, the nucleic acid is immobilised on a solid support.

In another aspect, the solid support is a cellulose based matrix.

In a further aspect, the solid matrix is selected from the group consisting of glass, glass fiber, glass microfiber, silica, silica gel, silica oxide, cellulose, nitrocellulose, carboxymethylcellulose, polyester, polyamide, carbohydrate polymers, polypropylene, polytetraflurorethylene, polyvinylidinefluoride, wool and porous ceramics. The solid matrix may comprise a glass or silica-based solid phase medium, a plastics-based solid phase medium or a cellulose-based solid phase medium. The solid support is preferably a cellulose-based matrix. Examples of cellulose-based matrices include FTA™ (data file 51668), 903 neonatal cards and 31-ETF cards available from GE Healthcare.

In one aspect, the solid support is in the form of a pre punched disc.

In another aspect, the solid support is in the form of an FTA pre punched disc.

In a further aspect, the lysis reagent is embedded onto said solid matrix.

In one aspect, the lysis reagent comprises an anionic surfactant or detergent. Sodium dodecyl sulphate (SDS) is an example of an anionic surfactant frequently used to lyse biological cells.

In another aspect, the amplification is carried out in a single reaction vessel such as a test tube or the well of a multi-well plate.

The method of the invention can be used either in a single reaction well or a high-throughput 96-well format in combination with automated sample processing as described by Baron et al., (2011, Forensics Science International: Genetics Supplement Series, 93, e560-e561). This approach would involve a minimal number of steps and increase sample throughput. The risk of operator-induced error, such as cross-contamination is also reduced since this procedure requires fewer manipulations compared to protocols associated with currently used, more labour intensive kits (e.g. QIAmp DNA blood mini kit, Qiagen). The risk of sample mix-up is also reduced since the procedure requires few manipulations. Importantly, the method is readily transferable to a multi-well format for high-throughput screening. The present invention can thus improve sample processing for carrying out PCR reactions to aid genetic interrogations. The invention can be conducted in a 96 well/high throughput format to facilitate sample handling and thus eliminate batch processing of samples.

The advantage of dried or lyophilised formulations of the polymerase chain reaction reagents is that they can be easily solubilised by the addition of water, thus saving operator time and facilitating operator usage. To minimise operator error, the dried reagent mixture can be pre-dispensed into the reaction vessel, such as the well of a multi-well plate. The preformulated, predispensed, ambient-temperature-stable beads or cakes allow amplification reactions to be carried out within a single well or reaction vessel and ensure greater reproducibility between reactions, minimize pipetting steps, and reduce the potential for pipetting errors and contamination.

According to a fourth aspect of the present invention, there is provided a method for detecting and/or quantifying amplified nucleic acid using a detection system comprising the steps:
  i) amplifying nucleic acids using the methods as hereinbefore described to produce amplified nucleic acid,
  ii) detecting the amplified nucleic acid, and
  iii) optionally quantifying the amplified nucleic acid.

In one aspect, the detection system is a PCR imaging system.

In another aspect, the detection system is a fluorescence or luminescent based system.

It will be understood that the nucleic acid may be viral, prokaryotic or eukaryotic in origin.

In one aspect, the nucleic acid sample is present in a cellular sample. The cellular sample may originate from a mammal, bird, fish or plant or a cell culture thereof. Preferably the cellular sample is mammalian in origin, most preferably human in origin. The sample containing the nucleic acid may be derived from any source. This includes, for example, physiological/pathological body fluids (e.g. secretions, excretions, exudates) or cell suspensions of humans and animals; physiological/pathological liquids or cell suspensions of plants; liquid products, extracts or suspensions of bacteria, fungi, plasmids, viruses, prions, etc.; liquid extracts or homogenates of human or animal body tissues (e.g., bone, liver, kidney, etc.); media from DNA or RNA synthesis, mixtures of chemically or biochemically synthesized DNA or RNA; and any other source in which DNA or RNA is or can be in a liquid medium.

In a further aspect, the method is for use as a tool selected from the group consisting of a molecular diagnostics tool, a human identification tool, a forensics tool, STR profiling tool and DNA profiling.

According to a fifth aspect of the present invention, there is provided a kit for amplifying nucleic acid comprising the dried reagent composition hereinbefore described and instructions for use thereof.

DETAILED DESCRIPTION OF THE INVENTION

Chemicals and Materials Used

A list of the chemicals and their sources is given below:
FTA papers for storing nucleic acid were obtained from GE Healthcare UK Limited;
Normal human blood (Tissue Solutions Ltd);
Genomic DNA (Promega product code G152A);
1 kb DNA ladder (Promega product code G571A);
Harris Uni-core punch, 1.2 mm (Sigma, Catalogue number Z708860-25ea, lot 3110);
OmniKlentaq Polymerase (Mo Bio Inc, catalogue code 1225-250);
Deoxyribonucleotide triphosphate (dNTP) (Life Tech);
PCR Grade Bovine Serum Albumin (Life Tech);
Forward and reverse β-globin primer (Sigma Genosys) β-globin 1.3 forward 5'-TTAGGCCTTAGCGGGCT-TAGAC-3' (Seq ID No. 1) and β-globin 1.3 reverse 5'-CCAGGATTTTTGATGGGACACG-3' (Seq ID No. 2));
α-cyclodextrin (Fluka code 28705) and
Sterile water (Sigma Product code W4502).

Excipient mix:
Ficoll 70 (GE Healthcare);
Ficoll 400 (GE Healthcare) and
Melezitose (Sigma)
Cycle Sequence Mix 10×:
Trizma (Sigma);
KCl (Sigma);
MgCl (Sigma) and
Nuclease-free water (Sigma)
Exchange buffer:
Tris/HCl pH8.5 (Sigma);
1M CaCl2 (Sigma);
1.0M MgCl2 (Sigma);
2.0M KCl (Sigma) and
RHODAFAC RE-960 (7% RE960) (Kao Chemicals)

Experimental Results

DNA measurement from dried blood spots from cellulose matrices using qPCR.

PCR reagents were combined with cyclodextrin and lyophilised under the following conditions in Table 1.

TABLE 1

| Lyophilisation conditions | | | |
|---|---|---|---|
| Temperature (° C..) | Vacuum (mTorr) | Time (min.) | Comment |
| −46 | 100 | 600 | hold |
| −36 | 100 | 250 | ramp |
| −36 | 100 | 300 | hold |
| 0 | 100 | 300 | hold |
| 28 | 100 | 233 | ramp |
| 28 | 100 | 360 | hold |
| Post Heat: | | | |
| 28 | 100 | 2000 | hold |

Samples were combined with the lyophilised nucleic acid amplification composition in a 96 well plate.

PCR Reaction was Set Up as Follows:

Blood-spotted FTA was added to a well with a nucleic acid amplification reagent cake that contained cyclodextrin or did not contain cyclodextrin. Standards and samples were added to the appropriate wells. The plates were centrifuged at 1000 rpm for 1 minute and sealed. PCR was carried out on an MJ Research PTC-200 Thermo Cycler following the manufacturer's user instructions.

The thermal cycling conditions were: 95° C. for 5 min, 95° C. for 30 sec, 55/65° C. for 1 min, 72° C. for 2 min followed by 35 cycles of: 95° C. for 30 sec, 55/65° C. for 1 min, 72° C. 2 min, followed by 72° C. for 10 mins.

Following amplification, visualisation of PCR products was achieved using agarose gel electrophoresis (1×TEA buffer, 1% agarose gel).

The standard well of the 96 well PCR plate was loaded with 50 of the 1 Kb DNA ladder with 10 of 6× loading buffer.

Figure 1:
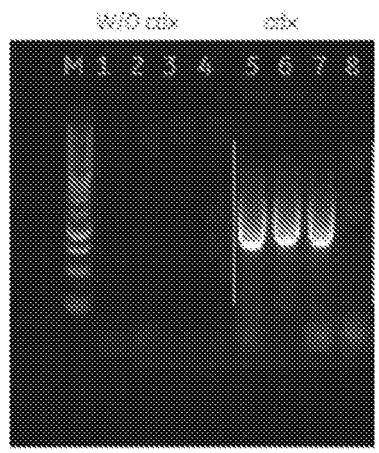
FIG. 1: Presents the results from PCR amplification of unwashed blood-spotted FTA paper with nucleic acid amplification reagent cakes with or without α-cyclodextrin.
Figure 2:
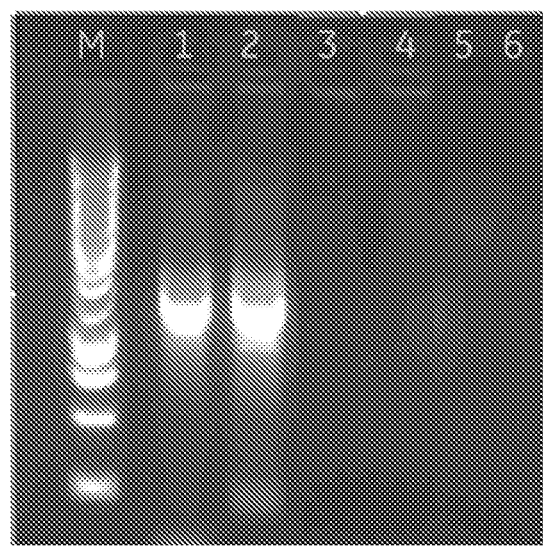
FIG. 2: Presents the results from PCR amplification of unwashed blood-spotted FTA paper with nucleic acid amplification reagent cakes with α-cyclodextrin.
Figure 3:
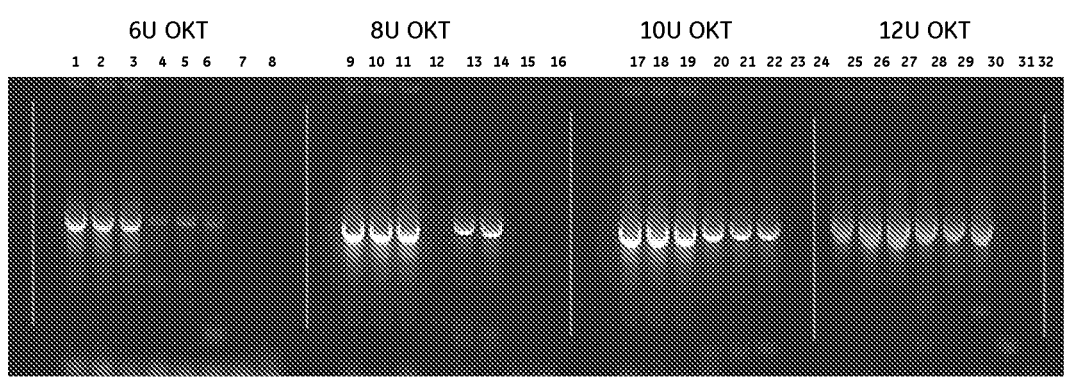
FIG. 3: Presents results from PCR amplification of titrated OmniKlen Taq (OKT) polymerase, in nucleic acid amplification reagent cakes, demonstrating the best concentration to freeze dry the nucleic acid amplification formulation.

The results are presented in FIGS. 1, 2 and 3.

FIG. 1 shows PCR amplification of unwashed blood-spotted FTA with the lyophilised nucleic acid amplification composition with or without α-cyclodextrin: Lane M: 1 kb Ladder; Lane 1-4: FTA punch spotted with whole blood (1.2 mm) with a lyophilised nucleic acid amplification composition without cyclodextrin; Lane 5-8: FTA punch spotted with whole blood (1.2 mm) with the lyophilised nucleic acid amplification composition containing cyclodextrin.

FIG. 2 shows PCR amplification of unwashed blood-spotted FTA with the lyophilised nucleic acid amplification composition with or without α-cyclodextrin: Lane M: 1 kb Ladder; Lane 1-2: FTA punch spotted with whole blood (1.2 mm) with the lyophilised nucleic acid amplification composition containing cyclodextrin; Lane 3-4: FTA punch (1.2 mm) with the lyophilised nucleic acid amplification composition containing cyclodextrin; Lane 5-6: FTA punch spotted with whole blood (1.2 mm) with the lyophilised nucleic acid amplification composition without cyclodextrin.

FIG. 3 shows PCR amplification of unwashed blood-spotted FTA with the lyophilised nucleic acid amplification composition without α-cyclodextrin and with varying concentrations of OKT Taq polymerase: Lane 1-8 contains 6 U OKT, Lane 1-3 FTA punch spotted with whole blood, Lane 4-6 genomic DNA, Lane 7-8 no DNA template; Lane 9-16 contains 8 U OKT, Lane 9-11 FTA punch spotted with whole blood, Lane 12-14 genomic DNA, Lane 15-16 no DNA template; Lane 17-24 contains 10 U OKT, Lane 17-19 FTA punch spotted with whole blood, Lane 20-22 genomic DNA, Lane 23-24 no DNA template; Lane 25-32 contains 12 U OKT, Lane 25-27 FTA punch spotted with whole blood, Lane 28-30 genomic DNA, Lane 31-32 no DNA template.

TABLE 2

Concentration of reagents in the Excipient mix.

|  | Reagent Concentration in 1000 cakes |
|---|---|
| Ficoll 70 | 0.6933 g |
| Ficoll 400 | 0.6933 g |
| Melezitose | 1.083 g |
| 10x PCR Cycle sequence mix | 2.71 ml |
| 10% α-cyclodextrin | 2.855 ml |
| Nuclease-free water | 0 ml |

TABLE 3

Concentration of reagents in the Excipient mix without cyclodextrin.

|  | Reagent Concentration in 1000 cakes |
|---|---|
| Ficoll 70 | 0.6933 g |
| Ficoll 400 | 0.6933 g |
| Melezitose | 1.083 g |
| Cycle sequence mix 10x | 2.71 ml |
| 10% α-cyclodextrin | 0 ml |
| Nuclease-free water | 2.855 ml |

TABLE 4

Concentration of reagents in a 1000 ml of 10x PCR Cycle Sequence mix.

|  | Reagent Concentration in 1000 ml |
|---|---|
| 100 mM Trizma | 12.11 g |
| 500 mm KCl | 37.28 g |
| 15 mM MgCl | 3.05 g |
| Nuclease-free water | 0.95 L |

TABLE 5

Concentration of reagents in the Exchange buffer.

|  | Reagent Concentration in 1000 ml |
|---|---|
| 1.0M Tris/HCl pH8.5 | 20 ml |
| 1.0M CaCl$_2$ | 100 ml |
| 7% RE960 | 214.3 ml |
| 1.0M MgCl$_2$ | 2.5 ml |
| 2.0M KCl | 16.6 ml |
| Nuclease-free water | 746.5 ml |

TABLE 6

Concentration of reagents in the 8U OmniKlen Taq Polymerase lyophilised nucleic acid amplification composition.

|  | Reagent Concentration in 1000 cakes |
|---|---|
| Excipient Mix | 6.667 ml |
| 10 mg/ml BSA | 0.6 ml |
| 20 nM dNTPs | 0.25 ml |
| OmniKlen Taq polymerase | 0.08 ml |
| Primer | 0.4 pmoles/μl |
| Exchange buffer | 0.92 ml |
| Nuclease-free water | 1.483 ml |

TABLE 7

Concentration of reagents in the 6U OmniKlen Taq Polymerase lyophilised nucleic acid amplification composition.

|  | Reagent Concentration in 1000 cakes |
|---|---|
| Excipient Mix without cyclodextrin | 6.667 ml |
| 10 mg/ml BSA | 0.6 ml |
| 20 nM dNTPs | 0.25 ml |
| OmniKlen Taq polymerase | 0.06 ml |
| Primer | 0.4 pmoles/μl |
| Exchange buffer | 0.94 ml |
| Nuclease-free water | 1.483 ml |

TABLE 8

Concentration of reagents in the 10U OmniKlen Taq Polymerase lyophilised nucleic acid amplification composition.

|  | Reagent Concentration in 1000 cakes |
|---|---|
| Excipient Mix without cyclodextrin | 6.667 ml |
| 10 mg/ml BSA | 0.6 ml |
| 20 nM dNTPs | 0.25 ml |
| OmniKlen Taq polymerase | 0.1 ml |
| Primer | 0.4 pmoles/μl |
| Exchange buffer | 0.9 ml |
| Nuclease-free water | 1.483 ml |

TABLE 9

Concentration of reagents in the 12U OmniKlen Taq Polymerase lyophilised nucleic acid amplification composition.

| | Reagent Concentration in 1000 cakes |
|---|---|
| Excipient Mix without cyclodextrin | 6.667 ml |
| 10 mg/ml BSA | 0.6 ml |
| 20 nM dNTPs | 0.25 ml |
| OmniKlen Taq polymerase | 0.12 ml |
| Primer | 0.4 pmoles/µl |
| Exchange buffer | 0.92 ml |
| Nuclease-free water | 1.443 ml |

While preferred illustrative embodiments of the present invention are described, one skilled in the art will appreciate that the present invention can be practised by other than the described embodiments, which are presented for the purposes of illustration only and not by way of limitation. The present invention is limited only by the claims that follow.

The invention claimed is:

1. A method for nucleic acid amplification comprising:
   i) forming a solution comprising nucleic acid by contacting with water or a buffer a solid support having immobilized thereon the nucleic acid, wherein a lysis reagent is embedded onto said solid support, and wherein said solid support is a cellulose based matrix in the form of a pre punched disc;
   ii) adding a dried nucleic acid amplification reagent composition comprising cyclodextrin as a sequestering reagent lyophilized with a polymerase and a deoxyribonucleotide triphosphate (dNTP) to the solution,
   iii) incubating the solution with the dried nucleic acid amplification reagent composition; and
   iv) amplifying said nucleic acid,
   wherein the method does not include washing said solid support having immobilized thereon the nucleic acid.

2. The method of claim 1, wherein the nucleic acid amplification method is a polymerase chain reaction.

3. The method of claim 1, wherein the nucleic acid amplification method comprises reverse transcription polymerase chain reaction or isothermal amplification.

4. The method of claim 1, wherein said solution is formed by contacting water with the solid support having immobilized thereon the nucleic acid.

5. The method of claim 1, wherein the amplification is carried out in a single reaction vessel.

6. The method of claim 1, wherein said cyclodextrin is selected from a group consisting of α-cyclodextrin, β-cyclodextrin, γ-cyclodextrin, 6-O-α-D-Maltosyl-β cyclodextrin, hydroxyethyl-β-cyclodextrin, hydroxypropyl-β-cyclodextrin and 2-hydroxypropyl-β-cyclodextrin.

7. The method of claim 1, wherein said cyclodextrin is α-cyclodextrin.

8. The method of claim 1, wherein said dried nucleic acid amplification reagent composition further comprises at least one primer.

9. A method of detecting and/or quantifying amplified nucleic acid using a detection system comprising:
   i) amplifying nucleic acids using the method of claim 1 to produce amplified nucleic acid; and
   ii) detecting said amplified nucleic acid.

10. The method of claim 9, further comprising quantifying the amplified nucleic acid.

11. The method of claim 9, wherein said detection system is a PCR imaging system.

12. The method of claim 1, wherein the pre punched disc is an FTA pre punched disc.

* * * * *